US 6,589,175 B2

(12) United States Patent
Prater et al.

(10) Patent No.: US 6,589,175 B2
(45) Date of Patent: Jul. 8, 2003

(54) REAL-TIME ARBITRARY MMODE FOR ULTRASONIC IMAGING SYSTEM

(75) Inventors: David M Prater, Andover, MA (US); Janice Louise Frisa, Atkinson, NH (US); Jonathan Panek, Harvard, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/845,515

(22) Filed: Apr. 30, 2001

(65) Prior Publication Data

US 2002/0161299 A1 Oct. 31, 2002

(51) Int. Cl.[7] .................................................. A61B 8/00
(52) U.S. Cl. .................................................... 600/443
(58) Field of Search ................................ 600/443, 442, 600/437, 444, 455, 456, 457, 449, 432

(56) References Cited

U.S. PATENT DOCUMENTS

| | | | | |
|---|---|---|---|---|
| 5,515,856 A | * | 5/1996 | Olstad et al. ............... | 600/440 |
| 5,820,561 A | | 10/1998 | Olstad et al. ............... | 600/453 |
| 6,146,329 A | * | 11/2000 | Hayakawa ................... | 600/443 |
| 6,322,505 B1 | * | 11/2001 | Hossack et al. ............. | 600/437 |
| 6,352,507 B1 | * | 3/2002 | Torp et al. .................. | 600/438 |
| 6,354,997 B1 | * | 3/2002 | Holley et al. ............... | 600/440 |

FOREIGN PATENT DOCUMENTS

JP     08038475 A     2/1996     ........... G06F/15/62

OTHER PUBLICATIONS

ProSound SSD–5500 Pure HD product brochure.
R–FAM information—obtained from web site: http://www.aloka.ch/r–fam.htm.

* cited by examiner

Primary Examiner—Maulin Patel
Assistant Examiner—Marvin Lateef
(74) Attorney, Agent, or Firm—John Vodopia

(57) ABSTRACT

An ultrasonic imaging system having a real-time arbitrary mmode. A scan converter scan converts slices in real-time of a two-dimensional ultrasonic image which form an arbitrary user-defined curve within the two-dimensional ultrasonic image. The scan converted slices are used to display the curve as a time versus depth mmode image.

20 Claims, 6 Drawing Sheets

REAL-TIME ARBITRARY MMODE FOR ULTRASONIC IMAGING SYSTEM

BACKGROUND OF THE INVENTION

1. Field of the Invention

The present invention relates to an ultrasonic imaging system and, more particularly, to an ultrasonic imaging system having a real-time arbitrary mmode.

2. Description of the Related Art

Ultrasonic imaging systems are widely used to produce an image of the inside of a person's body.

FIG. 1 is a diagram illustrating the general concept of an ultrasonic imaging system. Referring now to FIG. 1, an ultrasonic imaging system 18 typically includes electronics 20 and a transducer 22. Electronics 20 produces control signals for a transducer 22. In accordance with the control signals, transducer 22 transmits ultrasonic energy 24 into tissue 26, such as that, for example, in a human body. Ultrasonic energy 24 causes tissue 26 to generate a signal 28 which is received by transducer 22. Electronics 20 then forms an image in accordance with the received signal 28.

There are many "modes" of operation for an ultrasonic imaging system.

FIG. 2 is a diagram illustrating scan lines in a conventional bmode, often referred to as brightness mode, of an ultrasonic imaging system. Referring now to FIG. 2, the ultrasonic imaging system produces a plurality of scan lines 30a through 30n. Generally, each scan line represents a narrow ultrasonic transmission and receipt of the generated signal in the direction of the scan line. Generally, the ultrasonic imaging system produces scan lines 30a–30n in sequential order to sweep across the intended target through a sufficient angle θ which might be, for example, 90°. Of course, FIG. 2 is only an example to illustrate bmode, and is not drawn to scale. Moreover, the number of scan lines and the specific angle θ are only intended as examples, and bmode is not limited by these examples.

Bmode provides only limited information. Therefore, an ultrasonic imaging system might also include a conventional mmode.

FIG. 3 is a diagram illustrating a conventional mmode display. Referring now to FIG. 3, a plurality of mmode scan lines 34a through 34x are displayed. Each mmode scan line 34a through 34x indicates depth into the target tissue. Although not shown in FIG. 3, each mmode scan line 34a through 34x uses a grey scale to indicate intensity in the depth direction.

Each mmode scan line 34a through 34x represents a scan of the same line through the target tissue, but taken at a different time. Therefore, the plurality of mmode scan lines 34a through 34x, taken together, provide information relating to depth into the target tissue over time for the same line. The above-described mmode may hereafter be referred to as "regular" mmode.

Bmode scan lines and regular mmode scan lines are displayed in real-time. Often, bmode and regular mmode are shown together on the same display, as these different modes, taken together, provide a significant amount of useful information in real-time.

FIG. 4 is a diagram illustrating a bmode display showing various organs within the human body. Referring now to FIG. 4, a bmode display 40, which is a two-dimensional ultrasonic image, might show, for example, a septum 42 inside a human body. Straight line 44 represents a specific mmode scan line which might be scanned over time as regular mmode. Then, a plurality of mmode scan lines taken over time along straight line 44 might be displayed as a regular mmode display such as that, for example, in FIG. 3.

As can be seen from FIG. 4, a regular mmode scan is taken along a straight line, such as straight line 44. However, for many reasons, it is desirable to provide an mmode scan along a user-defined curve, which might not be a straight line. For example, a user might desire to provide an mmode scan along curve 46 which more closely follows curves of tissue inside the human body.

Therefore, a conventional ultrasonic imaging system might include "arbitrary" mmode (often referred to as anatomical mmode). Arbitrary mmode is similar to regular mmode in that arbitrary mmode is a time versus depth display with gray scale used to show the intensity of the received signal. However, in arbitrary mmode, the data is acquired along a user defined curve within a two-dimensional ultrasonic image. For example, arbitrary mmode can provide data along curve 46 in FIG. 4.

However, while regular mmode is a real-time display, arbitrary mmode is not performed in real-time. Instead, arbitrary mmode is performed as a post-processing operation on stored two-dimensional images. This is a significant disadvantage of arbitrary mmode, as it would be much more preferable to perform arbitrary mmode in real-time.

Moreover, since arbitrary mmode is performed as a post-processing operation on stored two-dimensional images, the user is undesirably restricted to the two-dimensional frame rate for the time interval between arbitrary mmode lines.

SUMMARY OF THE INVENTION

Accordingly, the present invention provides an ultrasonic imaging system having a real-time arbitrary mmode.

Moreover, the present invention provides an apparatus including (a) a scan converter scan converting portions of slices in real-time of a two-dimensional ultrasonic image which form an arbitrary user-defined curve within the two-dimensional ultrasonic image; (b) an image buffer, the scan converter drawing the scan converted portions into the image buffer; and (c) a display displaying the curve as a time versus depth image from the scan converted portions drawn into the image buffer.

Further, the present invention provides a method including (a) producing a two-dimensional ultrasonic image; and (b) producing a real-time mmode image of ultrasonic data acquired along an arbitrary user-defined curve within the two-dimensional ultrasonic image.

The present invention also provides a method including (a) scan converting portions of slices in real-time of a two-dimensional ultrasonic image which form an arbitrary user-defined curve within the two-dimensional ultrasonic image; and (b) displaying the curve as a time versus depth image from the scan converted portions.

Additional advantages, features and embodiments of the invention will be set forth in part in the description which follows, and, in part, will be obvious from the description, or may be learned by practice of the invention.

BRIEF DESCRIPTION OF THE DRAWINGS

These and other objects and advantages of the invention will become apparent and more readily appreciated from the following description of the preferred embodiments, taken in conjunction with the accompanying drawings of which.

DESCRIPTION OF THE PREFERRED EMBODIMENTS

Figure 1:
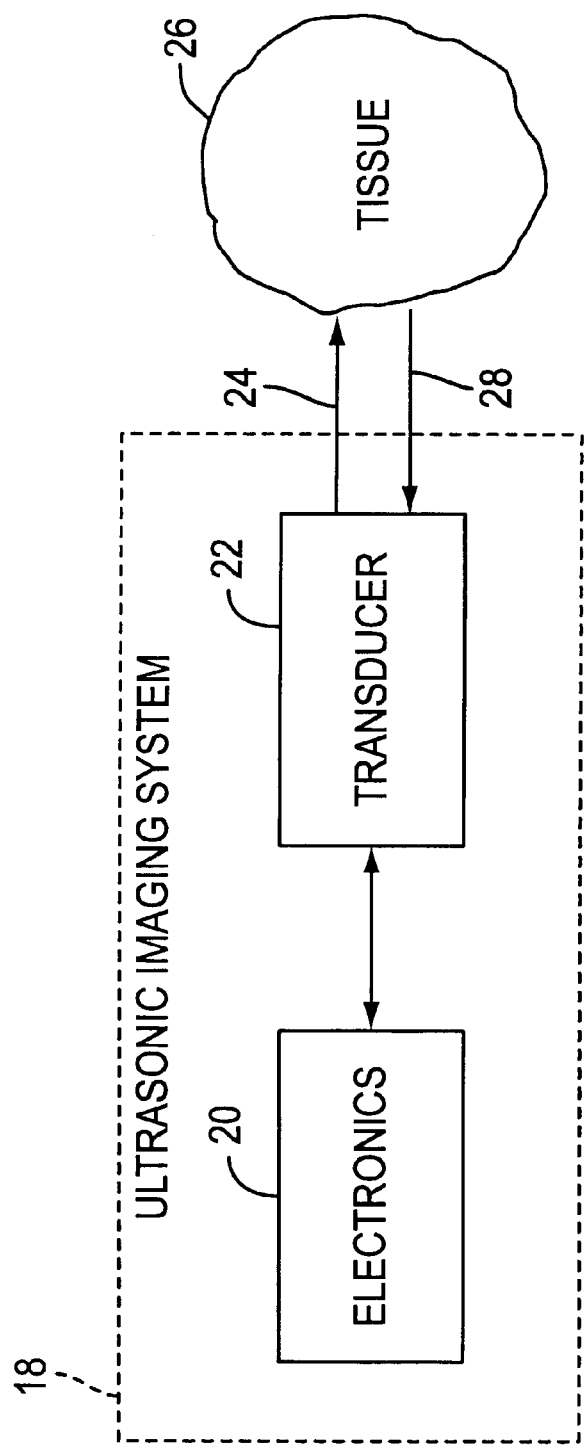
FIG. 1 (prior art) is a diagram illustrating the general concept of an ultrasonic imaging system.

Reference will now be made in detail to the present preferred embodiments of the present invention, examples of which are illustrated in the accompanying drawings, wherein like reference numerals refer to like elements throughout.

Figure 5A:
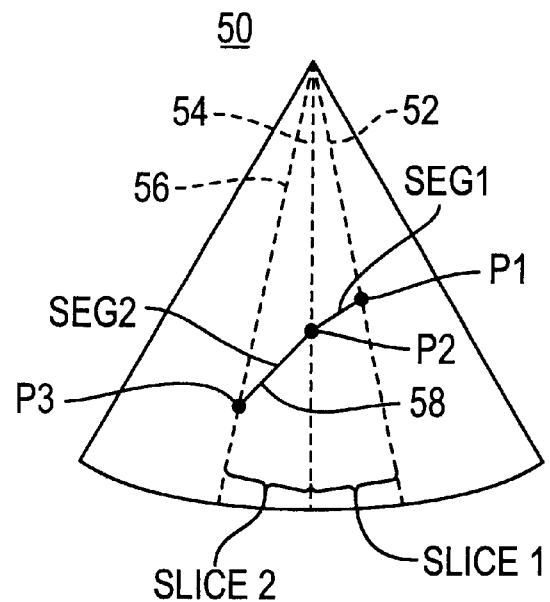
FIGS. 5(A) and 5(B) are diagrams illustrating real-time arbitrary mmode, according to an embodiment of the present invention.
Figure 5B:
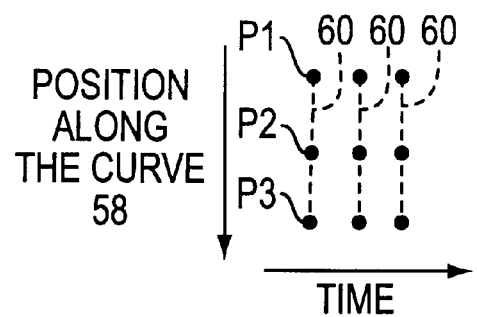

FIGS. 5(A) and 5(B) are diagrams illustrating real-time arbitrary mmode, according to an embodiment of the present invention. Referring now to FIG. 5(A), a two-dimensional ultrasonic image 50, such as that which might be produced, for example, in bmode, includes scan lines 52, 54 and 56. The entire area between scan lines 52 and 54 is referred to as slice 1, since this area represents a "slice" defined by scan lines 52 and 54. Similarly, the entire area between scan lines 54 and 56 is referred to as slice 2, since this area represents a "slice" defined by scan lines 54 and 56.

An arbitrary, user-defined curve 58 passes through point P1 on scan line 52, point P2 on scan line 54 and point P3 on scan line 56. Thus, one segment SEG1 of curve 58 is defined from points P1 to P2, and represents only a small portion of slice 1. Similarly, another segment SEG2 of curve 58 is defined from points P2 to P3, and represents only a small portion of slice 2.

As illustrated in FIG. 5(B), points P1 to P3 are plotted in as a straight, mmode scan line 60 taken at a specific time. A plurality of such mmode scan lines 60 are plotted for points P1 to P3 over time, to provide an arbitrary mmode display.

FIGS. 5(A) and 5(B) are not drawn to scale, and are exaggerated to show an underlying concept of the present invention. Instead, it should be understood that there are many scan lines which are very close together, and that curve 58 includes many segments that traverse many slices defined by scan lines.

Figure 6A:
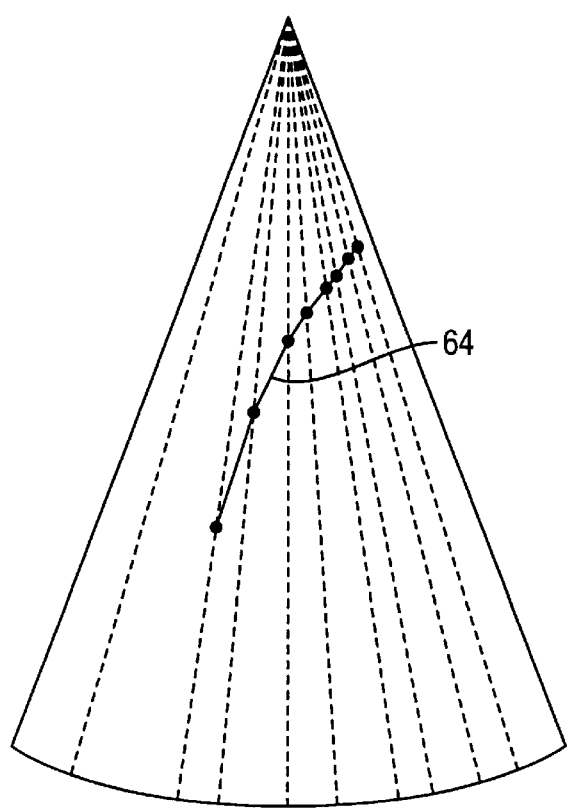
FIGS. 6(A) and 6(B) are diagrams illustrating a more complex embodiment of the present invention.
Figure 6B:
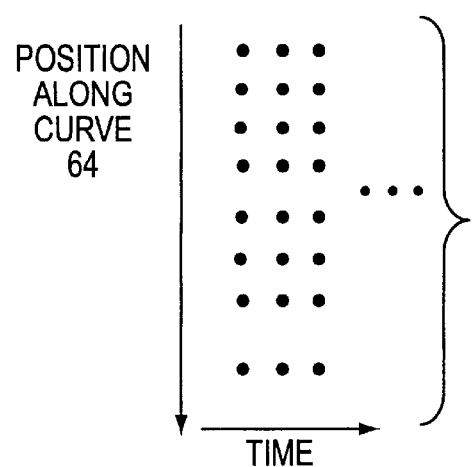

For example, FIGS. 6(A) and 6(B) are diagrams illustrating a more complex embodiment of the present invention. Referring now to FIG. 6(A), a user defined curve 64 traverses many scan lines. As illustrated in FIG. 6(B), the various points along curve 64 are plotted over time to provide an arbitrary mmode display.

Figure 7:
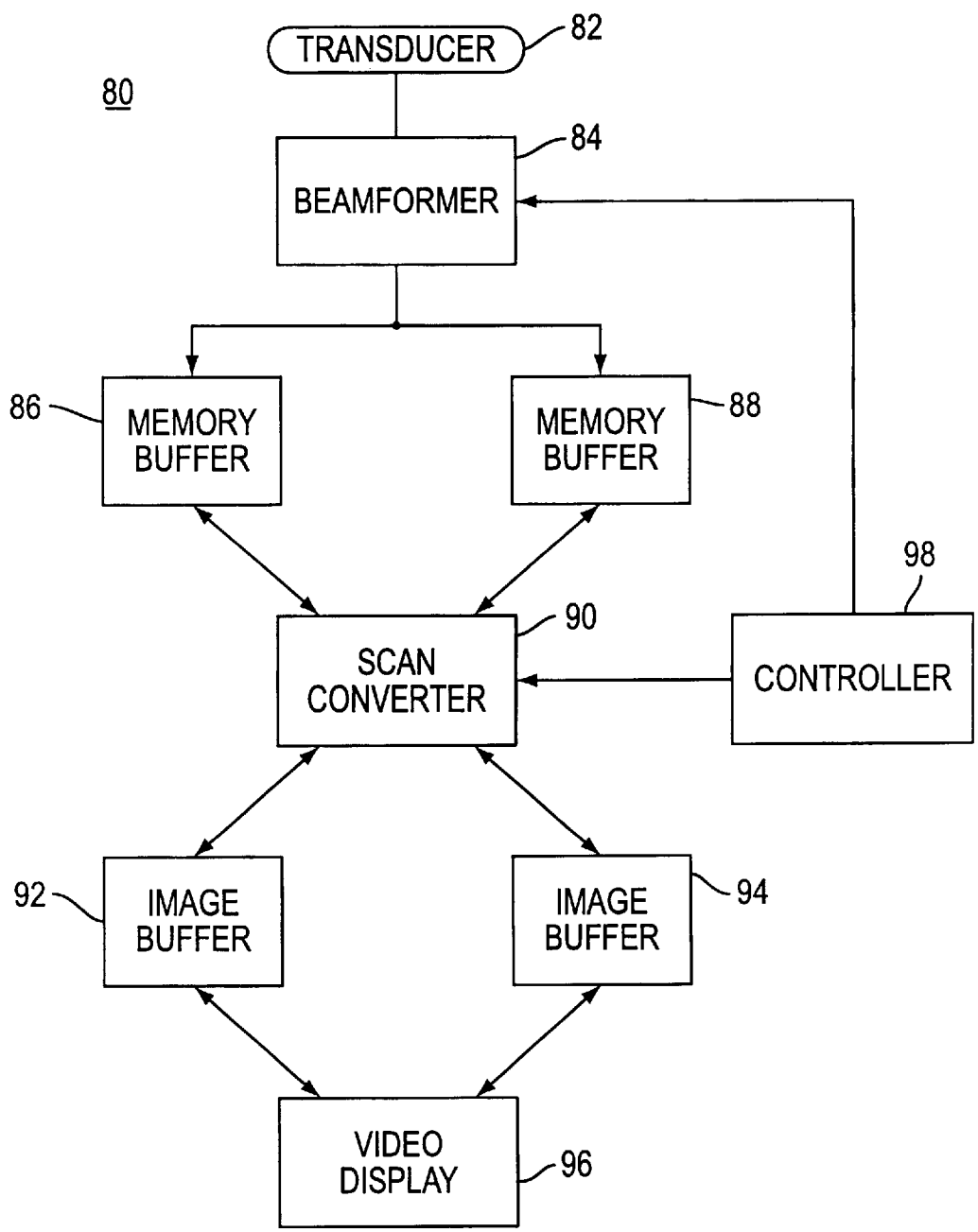
FIG. 7 is a diagram illustrating an ultrasonic imaging system which provides real-time arbitrary mmode, according to an embodiment of the present invention.

FIG. 7 is a diagram illustrating an ultrasonic imaging system which provides real-time arbitrary mmode, according to an embodiment of the present invention. Referring now to FIG. 7, an ultrasonic imaging system 80 includes a transducer 82 and a beamformer 84 which operate together to transmit ultrasonic energy into tissue (not illustrated in FIG. 7). The transmitted ultrasonic energy causes the tissue to generate a signal (not illustrated in FIG. 7) which is received by transducer 82 and appropriately processed by beamformer 84. Generally, beamformer 84 would be included in electronics 20 of FIG. 1.

Transducers and beamformers are well-known in the art, and will not be explained in detail here. Moreover, it should be understood that there are many different transducer/beamformer configurations. For example, some systems might have a transmit/receive switch which connects different transducers to beamformer 84 upon transmit and receive, respectively. Moreover, there might be some associated electronics used with transducer 82 and/or beamformer 84 which is not shown in FIG. 7. Therefore, it should be understood that the transducer/beamformer configuration shown in FIG. 7 is only one example, and the present invention is not limited to this example.

When producing a real-time arbitrary mmode display, a memory buffer 86 stores one frame of an mmode image corresponding to a user-defined curve along a two-dimensional ultrasonic image, such as, for example, curve 64 in FIG. 6(A). A memory buffer 88 then stores the next subsequent frame.

A scan converter 90 is coordinated with memory buffers 86 and 88 to scan convert the frames in sequence.

Therefore, beamformer 84 is coordinated with memory buffers 86 and 88 to alternately store sequential frames in memory buffers 86 and 88, and scan converter is coordinated with memory buffers 86 and 88 to alternately scan convert the frames in sequence.

There are many different ways to coordinate beamformer 84 with memory buffers 86 and 88, and to coordinate scan converter 90 with memory buffers 86 and 88, and the present invention is not limited to any particular manner. Moreover, although FIG. 7 shows only two memory buffers 86 and 88, the present invention is not limited to any specific number of memory buffers. Further, in a typical embodiment, there may be associated electronics for coordinating beamformer 84 with memory buffers 86 and 88, and for coordinating scan converter 90 with memory buffers 86 and 88, but which are not shown in FIG. 7.

Moreover, scan converter 90 is coordinated with image buffers 92 and 94 to alternately draw the scan converted frames into image buffers 92 and 94 in sequence. Similarly, image buffers 92 and 94 are coordinated with a video display 96 to display the user-defined curve as a time versus depth image from the scan converted frames drawn into image buffers 92 and 94.

There are many different ways to coordinate scan converter 90 with image buffers 92 and 94, and to coordinate video display 96 with image buffers 92 and 94, and the present invention is not limited to any particular manner. Moreover, although FIG. 7 shows only two image buffers 92 and 94, the present invention is not limited to any specific number of image buffers. Further, in a typical embodiment, there may be associated electronics for coordinating scan converter 90 with image buffers 92 and 94, and for coordinating video display 96 with image buffers 92 and 94, but which are not shown in FIG. 7.

Typically, a controller 98 would be provided to control beamformer 84 and scan converter 90.

It should be understood that the specific configuration of ultrasonic imaging system 80 shown in FIG. 7 is simply an example of an embodiment of the present invention, and the present invention is not limited to this specific embodiment.

With the configuration in FIG. 7, ultrasonic imaging system 80 can provide a real-time mmode image of a user-defined curve. The image is real-time, since scan converter 90 can perform the required scan conversion in real-time.

Scan converters are well-known. Generally, a scan converter is a well-known device which reads imaging information in one scanning format and converts it for display in another format. The present invention uses a scan converter to interpolate portions of slices defined by scan lines traversed by an arbitrary user-defined curve, where the interpolated portions form segments of the curve, to thereby provide a real-time arbitrary mmode.

Therefore, according to embodiments of the present invention, arbitrary mmode is provided by utilizing the capabilities of a scan converter, such as scan converter 90, to (1) scan convert portions of slices defined by different scan lines, where the portions form segments of a user-defined curve, and (2) draw the scan converted portions into arbitrary locations in image buffers 92 and 94. These two capabilities of a scan converter are combined by the present invention to allow the segments of the user defined mmode curve to be extracted and drawn in a time versus depth image.

Therefore, for example, scan converter 90 would typically be programmable to identify to scan converter 90 the following information: (a) which scan lines (for example, which two scan lines) define a respective slice, (b) which portion of the slice is to be scan converted, and (c) where on the screen the scan converted portion should be drawn.

This use of a scan converter in the present invention is significantly different than the conventional use of a scan converter. Conventionally, scan converters are used to scan convert an entire slice defined by two scan lines, and to display the entire slice as part of, for example, a bmode display. By contrast, as an example, various embodiments of the present invention use a scan converter to scan convert only a portion of the slice, as opposed to the entire slice, to provide real-time arbitrary mmode.

Moreover, with the present invention, real-time imaging can be optimized to provide a minimum mmode line update time as established by the number of scan lines traversed by the user-defined arbitrary curve. For example, assume that it takes a specific amount of time to shoot each scan line. This specific amount of time might be, for example, 250 $\mu$s. Assuming that, for example, a user-defined curve traverses six scan lines, then the ultrasonic imaging system can shoot six scan lines every 1.5 ms (6 times 250 $\mu$s equals 1.5 ms). Thus, the ultrasonic imaging system can shoot a new mmode line every 1.5 ms. In the remaining available time, the real-time two-dimensional image (for example, a bmode image) can be updated.

Further, with the present invention, a scan line sequence can be coordinated with scan converter 90 so that scanning to produce a two-dimensional ultrasonic image is interleaved with scanning for the mmode "wedge." Here, the mmode "wedge" is the set of scan lines which span the user-defined curve for the mmode scan. For example, assume that the user defines a curve which traverses eight (8) scan lines of a two-dimensional ultrasonic image, and that it takes 250 $\mu$s to shoot each scan line. Thus, the ultrasonic imaging system can shoot a new mmode line every 2 ms (8 times 250 $\mu$s equals 2 ms). Further, assume that the user sets a 5 ms update rate. This update rate provides for 3 ms (5 ms update rate minus 2 ms to shot an mmode line) in which to create the two-dimensional image. This 3 ms time would allow for twelve (12) scan lines to be shot (250 $\mu$s times 12 equals 3 ms).

Figure 2:
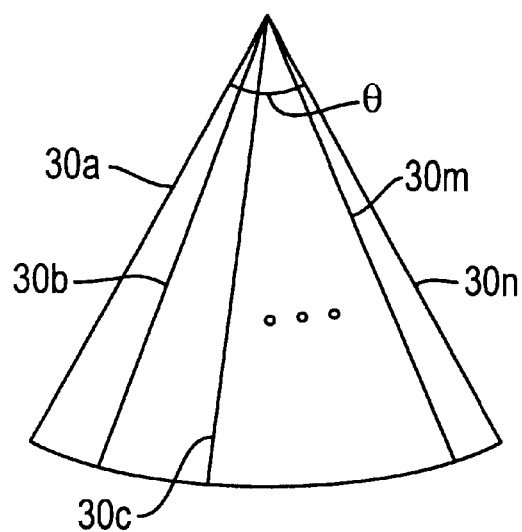
FIG. 2 (prior art) is a diagram illustrating scan lines in a conventional bmode of an ultrasonic imaging system.
Figure 3:
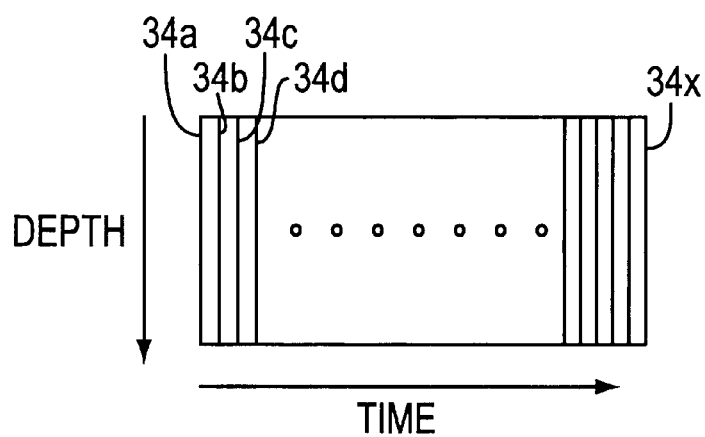
FIG. 3 (prior art) is a diagram illustrating a conventional mmode display.
Figure 4:
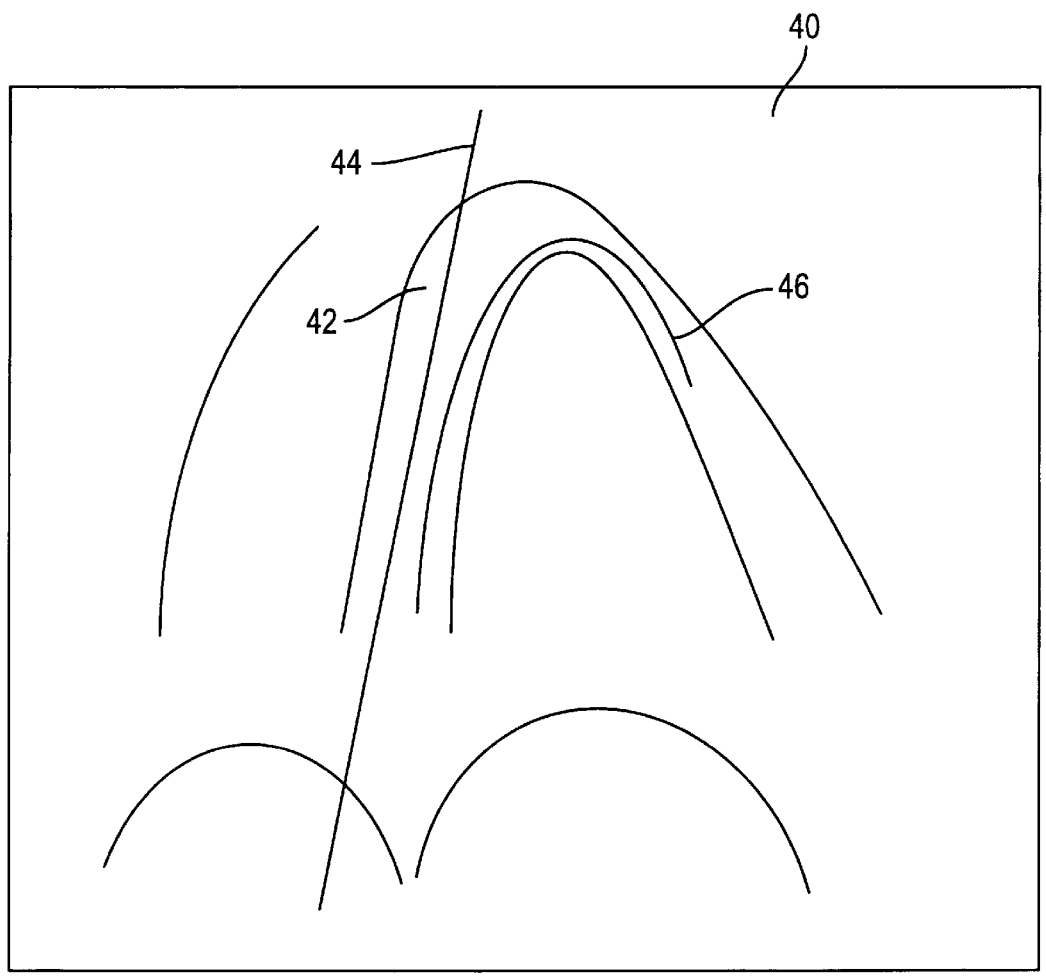
FIG. 4 (prior art) is a diagram illustrating a bmode display showing various organs within the human body.

Further, assume that there are one-hundred-twenty (120) scan lines in the two-dimensional image, which correspond, for example, to a 90° sector angle (see angle $\theta$ in FIG. 2) with the scan lines being ¾° apart. Shooting twelve (12) scan lines would cover an angle of 9° (12 times ¾° equals 9°).

Therefore, in this example, a scanning table for scan converter 90 might including the following information:
1. Shoot 12 scan lines at ¾° apart, starting at −45° and ending at −36°
2. Shoot 8 lines to produce one mmode line
3. Shoot 12 scan lines at ¾° apart, starting at −36° and ending at −27°
4. Shoot 8 lines to produce one mmode line
5. Shoot 12 scan lines at ¾° apart, starting at −27° and ending at −18°
6. Shoot 8 lines to produce one mmode line
7. Shoot 12 scan lines at ¾° apart, starting at −18° and ending at −9°
8. Shoot 8 lines to produce one mmode line
9. Shoot 12 scan lines at ¾° apart, starting at −9° and ending at 0°
10. Shoot 8 lines to produce one mmode line
11. Shoot 12 scan lines at ¾° apart, starting at 0° and ending at 9°
12. Shoot 8 lines to produce one mmode line
13. Shoot 12 scan lines at ¾° apart, starting at 9° and ending at 18°
14. Shoot 8 lines to produce one mmode line
15. Shoot 12 scan lines at ¾° apart, starting at 18° and ending at 27°
16. Shoot 8 lines to produce one mmode line
17. Shoot 12 scan lines at ¾° apart, starting at 27° and ending at 36°
18. Shoot 8 lines to produce one mmode line
19. Shoot 12 scan lines at ¾° apart, starting at 36° and ending at 45°
20. Shoot 8 lines to produce one mmode line Of course, the above table is only intended to illustrating the concept of a scanning table, and an actual scanning table might take a different format and/or include different information. Moreover, the various examples of angles, starting and ending points, times, etc, are only intended as examples, and the present invention is not limited to these examples. Instead, it should be understood that ultrasonic imaging allows for many different parameters to be used in creating ultrasonic images.

The present invention relates to "real-time" arbitrary mmode. Here, the term "real-time" indicates that a resulting display is created in real-time from the acquired data, as opposed to from stored images that were taken at a significantly earlier time than the display was created.

The present invention relates to an arbitrary mmode for a "user" defined curve. Here, a user refers to a person using the ultrasonic imaging system to take an ultrasonic image. Such a user would typically be an ultrasonic technician, a doctor or a nurse. However, the present invention is not limited to the user being any particular profession.

Further, there are many different ways in which a user can input information into an ultrasonic imaging system to define a curve. For example, the ultrasonic imaging system may allow the user to enter coordinates for the curve and/or use a trackball or computer mouse to define the curve. Also, for example, the ultrasonic imaging system might have a touch screen or a voice interface allowing the user to define a curve. These are only examples, and the present invention is not limited to any specific manner in which the user defines a curve.

The present invention relates to a "grey scale" used with an mmode display. However, the present invention is not limited to the use of a grey scale. For example, various colors, instead of a black/white grey scale, may be used.

There are different types of mmode, and the present invention is not limited to any specific type of mmode. For example, generally, the above description specifically relates to black-white mmode, where the mmode is made from the same type of lines as the bmode image. However, another use of arbitrary mmode is to form the mmode line from a two-dimensional color flow image. The color flow image is similar to the bmode image in that it is a two-dimensional image. It differs in that each line of the color flow image is formed by processing multiple scan lines at the same location. Thus, the present invention is applicable to various types of mmode, such as, for example, mmode formed from a color flow image.

Although a few preferred embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An ultrasonic imaging system having a real-time arbitrary mmode producing a real-time display of ultrasonic data acquired along an arbitrary user-defined curve within a two-dimensional image, comprising:
    generating means for generating different scan lines from a two-dimensional ultrasonic image, a slice being formed between each adjacent pair of scan lines, an arbitrary curve traversing the scan lines being defined by a user such that the curve is formed from an assembly of slice portions each being a portion of a slice traversed by the arbitrary user-defined curve; and
    a scan converter arranged to scan convert only the slice portions in real-time so that a real-time display of ultrasonic data acquired along the arbitrary user-defined curve is displayable from the scan converted portions.

2. An ultrasonic imaging system as in claim 1, further comprising:
    an image buffer, the scan converter being arranged to draw the scan converted portions into the image buffer; and
    a display displaying the curve as a time versus depth image from the scan converted portions drawn into the image buffer.

3. An ultrasonic imaging system as in claim 2, wherein a scan line sequence is coordinated with the scan converter so that scanning to produce the two-dimensional ultrasonic image is interleaved with scanning to produce an image by the mmode.

4. An ultrasonic imaging system as in claim 1, wherein a scan line sequence is coordinated with the scan converter so that scanning to produce the two-dimensional ultrasonic image is interleaved with scanning to produce an image by the mmode.

5. An ultrasonic imaging system as in claim 1, wherein the two-dimensional image is updated in real-time by the ultrasonic imaging system in accordance with a minimum mmode update time established by a number of scan lines in the two-dimensional ultrasonic image traversed by the curve.

6. An ultrasonic imaging system as in claim 1, wherein the generating means comprise a transducer and beamformer operating together to obtain ultrasonic images.

7. An ultrasonic imaging system as in claim 1, further comprising:
    image buffers, the scan converter drawing the scan converted portions into the image buffers in sequence; and
    a display displaying the curve as a time versus depth image from the scan converted portions drawn into the image buffers.

8. An ultrasonic imaging system having a real-time arbitrary mmode producing a real-time display of ultrasonic data acquired along an arbitrary user-defined curve within a two-dimensional image, comprising:
    memory buffers for storing different frames of an mmode image for the curve;
    a scan converter coordinated with the memory buffers to scan convert the frames in real-time;
    image buffers, the scan converter being coordinated with the image buffers to draw the scan converted frames into the image buffers; and
    a display displaying the curve as a time versus depth image from the scan converted frames drawn into the image buffers to thereby provide a real-time mmode image of the curve.

9. An ultrasonic imaging system as in claim 8, wherein a scan line sequence is coordinated with the scan converter so that scanning to produce the two-dimensional ultrasonic image is interleaved with scanning to produce the mmode image.

10. An apparatus for generating real-time arbitrary mmode images, the apparatus comprising:
    a scan converter scan converting portions of slices in real-time of a two-dimensional ultrasonic image which form an arbitrary user-defined curve within the two-dimensional ultrasonic image;
    image buffers, the scan converter being coordinated with the image buffers to alternately draw the scan converted portions into the image buffers in sequence; and
    a display coordinated with the image buffers to display the curve as a time versus depth image from the scan converted portions drawn into the image buffers, wherein the displayed image is a real-time arbitrary mmode image.

11. A method comprising:
    providing an ultrasonic imaging system having a real-time arbitrary mmode,
    the ultrasonic imaging system including a transducer and a beamformer operating together to obtain ultrasonic images, memory buffers for storing frames of an mmode image corresponding to a user-defined curve along an ultrasonic image obtained by the transducer and beamformer, a scan converter for scan converting sequential frames stored in the memory buffers in real-time, image buffers coordinated with the scan converter such that the scan converter alternately draws the scan converted frames into the image buffers in sequence, and a display coordinated with the image buffers to display the curve as a time versus depth image from the scan converted frames drawn into the image buffers.

12. A method comprising:
    producing a two-dimensional ultrasonic image;
    generating different scan lines from the two-dimensional ultrasonic image;
    forming a slice between each adjacent pair of scan lines;
    defining an arbitrary curve traversing the scan lines to thereby form the curve from an assembly of slice portions, each slice portion being a portion of a slice traversed by the arbitrary curve; and
    scan converting the slice portions in real-time so that the curve is displayable from the scan converted portions.

13. A method as in claim 12, further comprising:
    displaying the curve as a time versus depth image from the scan converted portions.

14. A method as in claim 13, further comprising coordinating a scan line sequence with said scan converting so that scanning to produce the two-dimensional ultrasonic image is interleaved with scanning to produce the mmode image.

15. A method as in claim 12, further comprising coordinating a scan line sequence with said scan converting so that scanning to produce the two-dimensional ultrasonic image is interleaved with scanning to produce the mmode image.

16. A method as in claim 12, further comprising updating the two-dimensional ultrasonic image in real-time in accordance with a minimum mmode update time established by a number of scan lines in the two-dimensional ultrasonic image traversed by the curve.

17. A method for generating real-time arbitrary mode images, the method comprising:

scan converting only portions of slices in real-time of a two-dimensional ultrasonic image which form an arbitrary user-defined curve within the two-dimensional ultrasonic image; and displaying the curve as a time versus depth image from the scan converted portions, wherein the displayed image is a real-time arbitrary mmode image.

18. A method as in claim 17, further comprising alternately drawing the scan converted portions into image buffers in sequence, the curve being displayed as a time versus depth image from the scan converted portions drawn into the image buffers.

19. An apparatus comprising:

an ultrasonic imaging system including a transducer and a beamformer operating together to obtain ultrasonic images, memory buffers for storing frames of an mmode image corresponding to a user-defined curve along an ultrasonic image obtained by the transducer and beamformer, a scan converter for scan converting sequential frames stored in the memory buffers in real-time, image buffers coordinated with the scan converter such that the scan converter alternately draws the scan converted frames into the image buffers in sequence, and display means for displaying ultrasonic images in a real-time arbitrary mmode, the display means being coordinated with the image buffers to display the curve as a time versus depth image from the scan converted frames drawn into the image buffers.

20. A method comprising:

producing a two-dimensional ultrasonic image;

producing a real-time mmode image of ultrasonic data acquired along an arbitrary user-defined curve within the two-dimensional ultrasonic image, wherein the produced image is a real-time arbitrary mmode image; and updating the two-dimensional ultrasonic image in real-time in accordance with a minimum mmode update time established by a number of scan lined in the two dimensional ultrasonic image traversed by the curve.

\* \* \* \* \*